(12) United States Patent
Stubber

(10) Patent No.: US 9,993,264 B2
(45) Date of Patent: Jun. 12, 2018

(54) SURGICAL TROCAR

(71) Applicant: RESEARCH MEDICAL PTY LTD, Sorrento (AU)

(72) Inventor: Raymond Lawrence Stubber, Sorrento (AU)

(73) Assignee: Research Medical Pty Ltd., Sorrento (AU)

( * ) Notice: Subject to any disclaimer, the term of this patent is extended or adjusted under 35 U.S.C. 154(b) by 753 days.

(21) Appl. No.: 14/362,846

(22) PCT Filed: Dec. 7, 2012

(86) PCT No.: PCT/AU2012/001502
§ 371 (c)(1),
(2) Date: Jun. 4, 2014

(87) PCT Pub. No.: WO2013/082671
PCT Pub. Date: Jun. 13, 2013

(65) Prior Publication Data
US 2014/0364889 A1    Dec. 11, 2014

(30) Foreign Application Priority Data
Dec. 7, 2011   (AU) ................................ 2011905092

(51) Int. Cl.
*A61B 17/34*    (2006.01)
*A61B 17/00*    (2006.01)
(52) U.S. Cl.
CPC .. *A61B 17/3415* (2013.01); *A61B 2017/0042* (2013.01); *A61B 2017/00429* (2013.01);
(Continued)

(58) Field of Classification Search
CPC ...... A61B 17/3415; A61B 2017/00429; A61B 2017/00455; A61B 2017/0042; A61B 2217/005; A61M 5/158; A61M 2005/1581
(Continued)

(56) References Cited

U.S. PATENT DOCUMENTS 1,235,587 A  *  8/1917  Moffatt .................. D05B 85/00
112/222
1,323,340 A  *  12/1919  Weis ...................... D05B 85/00
112/222
(Continued)

FOREIGN PATENT DOCUMENTS

EP      0769278 A2   4/1997
GB      2103936 A    3/1983
(Continued)

OTHER PUBLICATIONS

English translation of Japanese patent application JP 19890157260. Applicant is Nippon Medical Supply and entitled Fitting Structure of Medical Soft Tube with Hard Member, published Jan. 30, 1991 published as JPH0321263(A).
(Continued)

*Primary Examiner* — Amy R Weisberg
(74) *Attorney, Agent, or Firm* — Charles H Jew

(57) ABSTRACT

A surgical trocar 10 has an elongate shaft 12 with a leading point or edge 28 for piercing flesh and a thumb grip region 22 at an inner bend region 18. The grip region may include a flat zone and can be integral with the shaft, optionally stamped or pressed into the material of the shaft.

23 Claims, 5 Drawing Sheets

(52) U.S. Cl.
CPC ............... *A61B 2017/00455* (2013.01); *A61B 2217/005* (2013.01)

(58) Field of Classification Search
USPC ........................................................ 606/185
See application file for complete search history.

(56) References Cited

U.S. PATENT DOCUMENTS

| | | | | |
|---|---|---|---|---|
| 2,421,339 A * | 5/1947 | Leger | ................... | F41B 13/08 16/430 |
| 3,397,660 A * | 8/1968 | Luther | ................... | D05B 85/00 112/222 |
| 3,479,708 A * | 11/1969 | Foster | ................... | D04H 18/02 28/115 |
| 3,769,980 A * | 11/1973 | Karman | ................... | A61B 1/32 600/220 |
| 3,815,798 A * | 6/1974 | Lavitch | ................ | A41H 37/008 223/102 |
| 3,818,630 A * | 6/1974 | May | ....................... | A63H 33/40 446/396 |
| 4,128,067 A * | 12/1978 | Zocher | ................... | D05B 85/00 112/222 |
| 4,195,584 A * | 4/1980 | Falk | ....................... | D05C 15/20 112/222 |
| 4,236,520 A * | 12/1980 | Anderson | ................ | A61D 1/02 119/14.21 |
| 4,490,136 A * | 12/1984 | Ekbladh | ............. | A61B 17/3415 604/22 |
| 4,863,441 A * | 9/1989 | Lindsay | ................ | A61M 25/00 604/264 |
| 4,883,474 A * | 11/1989 | Sheridan | ............... | A61M 1/008 604/272 |
| 5,046,438 A * | 9/1991 | Hakui | .................... | D05C 15/20 112/222 |
| 5,180,385 A * | 1/1993 | Sontag | ............... | A61B 17/0482 606/223 |
| 5,484,417 A * | 1/1996 | Waitz | ................. | A61B 17/3417 604/164.11 |
| 5,492,538 A * | 2/1996 | Johlin, Jr. | ......... | A61M 25/0068 128/899 |
| 5,554,138 A * | 9/1996 | Stanford | ........... | A61M 25/0068 600/583 |
| 5,569,301 A * | 10/1996 | Granger | ............ | A61B 17/0625 606/223 |
| 5,693,030 A * | 12/1997 | Lee | .................... | A61M 25/0068 604/117 |
| 5,725,555 A * | 3/1998 | Moll | ................ | A61B 17/06066 606/222 |
| 5,807,317 A | 9/1998 | Krech | | |
| 5,876,383 A * | 3/1999 | Grooters | ........... | A61M 25/0068 604/264 |
| 6,042,576 A * | 3/2000 | DeVries | .............. | A61M 25/007 604/264 |
| 6,168,611 B1 * | 1/2001 | Rizvi | ..................... | A61B 17/06 606/222 |
| 6,186,987 B1 * | 2/2001 | Grooters | ........... | A61M 25/0068 604/264 |
| 6,460,256 B2 * | 10/2002 | Peppel | ................. | B25G 1/102 30/340 |
| 8,292,920 B2 * | 10/2012 | Dabir | ............... | A61B 17/06061 606/148 |
| 8,795,308 B2 * | 8/2014 | Valin | ............... | A61B 17/06066 606/167 |
| 8,888,690 B2 * | 11/2014 | Swinehart | ........ | A61B 17/00234 600/184 |
| 8,926,636 B2 * | 1/2015 | Robertson | ........ | A61B 17/06109 128/834 |
| 2001/0018576 A1 * | 8/2001 | Quinn | ............... | A61M 25/0069 604/264 |
| 2001/0037092 A1 * | 11/2001 | Amar | ...................... | A61M 5/32 604/264 |
| 2002/0026156 A1 * | 2/2002 | Quinn | ................. | A61M 25/003 604/264 |
| 2002/0058959 A1 * | 5/2002 | Gellman | ............ | A61B 17/0401 606/185 |
| 2002/0173689 A1 * | 11/2002 | Kaplan | .............. | A61B 17/3468 600/7 |
| 2003/0208154 A1 * | 11/2003 | Close | .................... | A61B 5/153 604/65 |
| 2004/0002724 A1 * | 1/2004 | Falahee | .............. | A61B 17/3415 606/185 |
| 2005/0101984 A1 * | 5/2005 | Chanduszko | ...... | A61B 17/0057 606/185 |
| 2006/0106277 A1 * | 5/2006 | Romero Maroto | ........... | A61B 17/06066 600/37 |
| 2007/0078396 A1 * | 4/2007 | Feeley | ............... | A61B 17/3415 604/164.01 |
| 2007/0197981 A1 * | 8/2007 | Abe | ................. | A61B 17/06066 604/272 |
| 2008/0275473 A1 * | 11/2008 | Filipi | ................. | A61B 17/0469 606/145 |
| 2010/0222641 A1 * | 9/2010 | Chu | ................. | A61B 17/06109 600/30 |
| 2010/0280368 A1 * | 11/2010 | Can | .................... | A61B 1/00071 600/431 |
| 2011/0072859 A1 * | 3/2011 | Dietz | ..................... | D04B 35/06 66/120 |
| 2011/0112566 A1 * | 5/2011 | Maurer | ............ | A61B 17/06066 606/185 |
| 2012/0089166 A1 * | 4/2012 | Modesitt | ........... | A61B 17/0057 606/185 |
| 2012/0123471 A1 * | 5/2012 | Woodard, Jr. | ... | A61B 17/06004 606/223 |
| 2012/0136381 A1 * | 5/2012 | Morrison | ........... | A61B 17/3417 606/185 |
| 2012/0221032 A1 * | 8/2012 | Duperier | ............ | A61B 17/3211 606/170 |
| 2014/0163481 A1 * | 6/2014 | Cornell | ................. | A61M 35/00 604/264 |
| 2014/0364889 A1 * | 12/2014 | Stubber | .............. | A61B 17/3415 606/185 |
| 2015/0142040 A1 * | 5/2015 | Kawaura | .......... | A61B 17/06109 606/185 |
| 2015/0327974 A1 * | 11/2015 | Allen | .................... | A61F 2/0045 600/37 |

FOREIGN PATENT DOCUMENTS

| | | |
|---|---|---|
| WO | 2004016184 A1 | 2/2004 |
| WO | 2009137761 A2 | 11/2009 |

OTHER PUBLICATIONS

English translation of Japanese patent application JP 20040053622. Applicant is Sumitomo Bakelite Co. and entitled Medical Needle, published Sep. 8, 2005 published as JP2005237763 (A).

English translation of Japanese patent application JP 19930012147U. Published as JPH0670706 (U) Oct. 4, 1994.

* cited by examiner

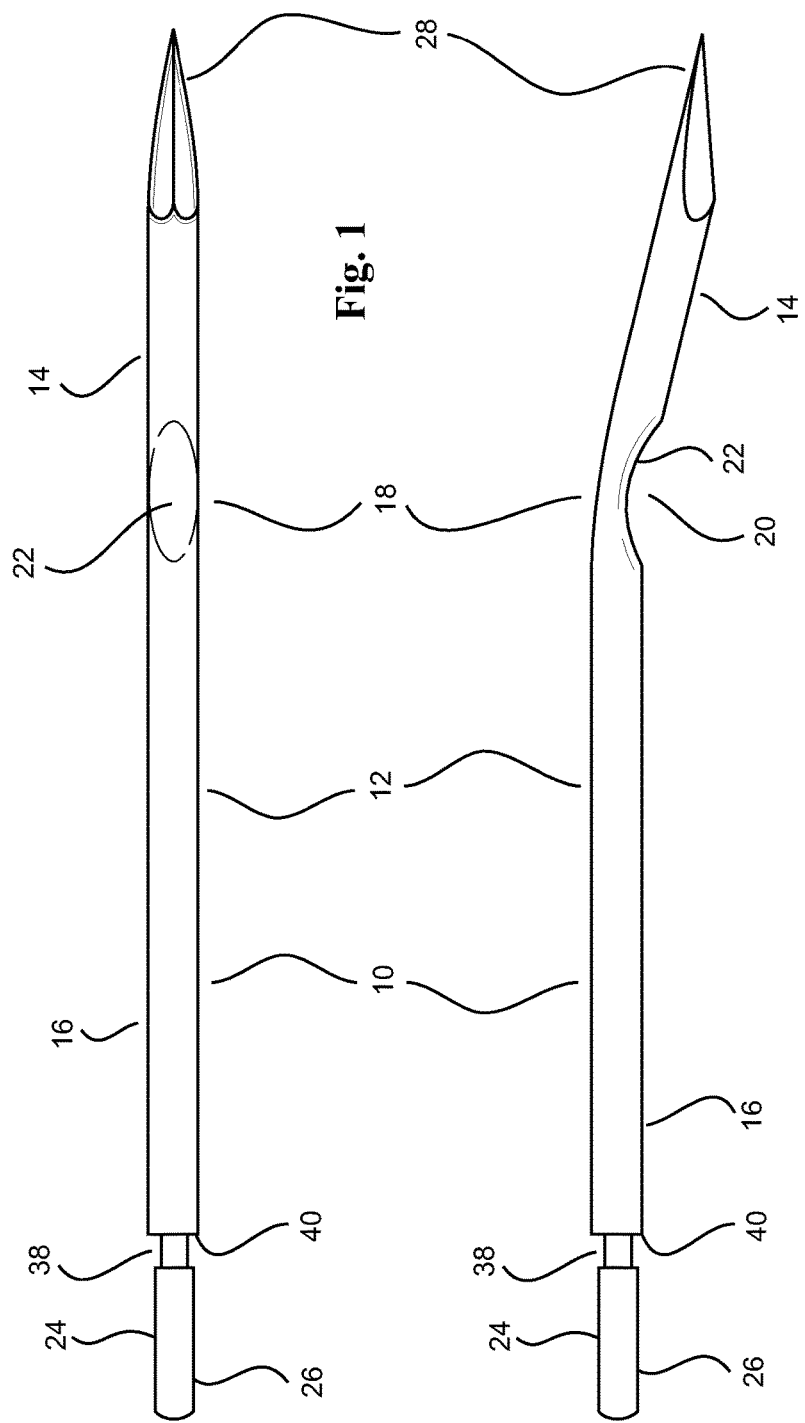

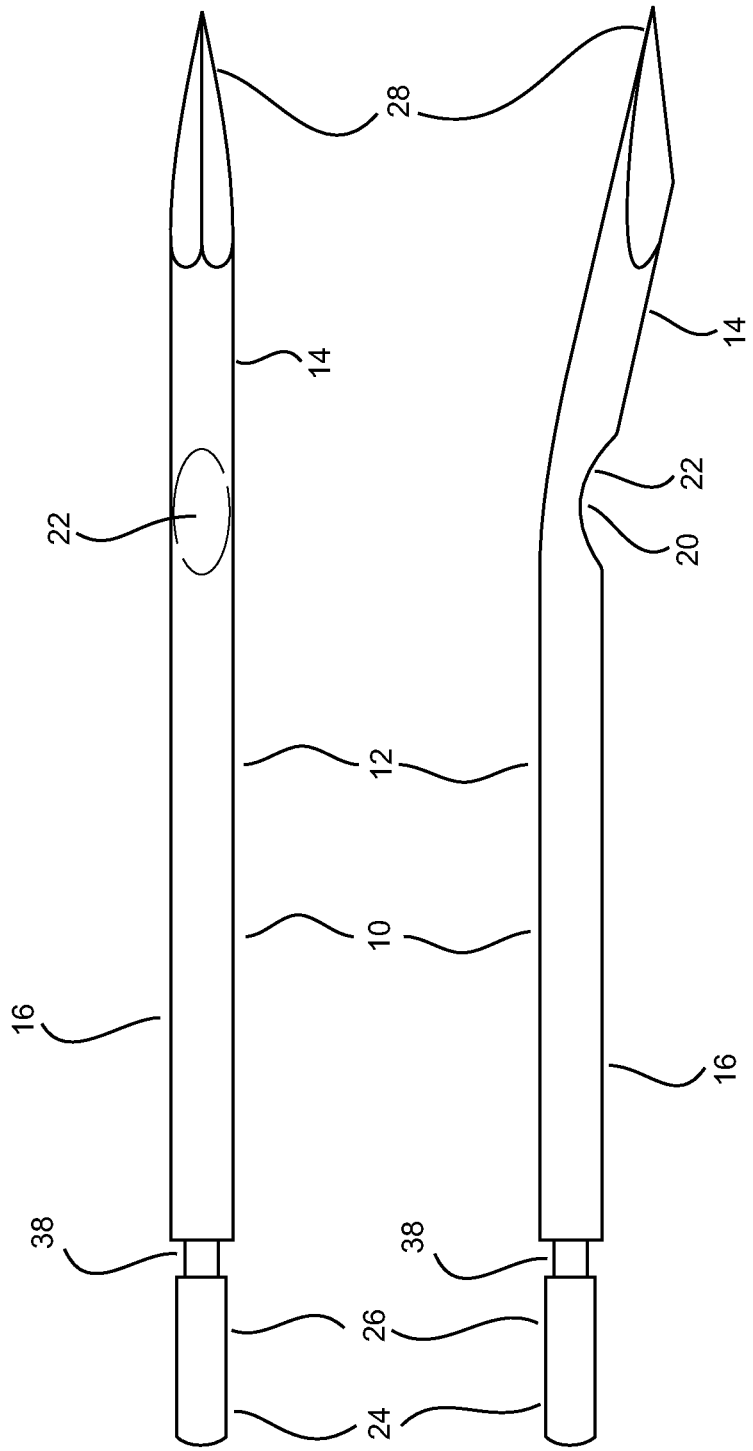

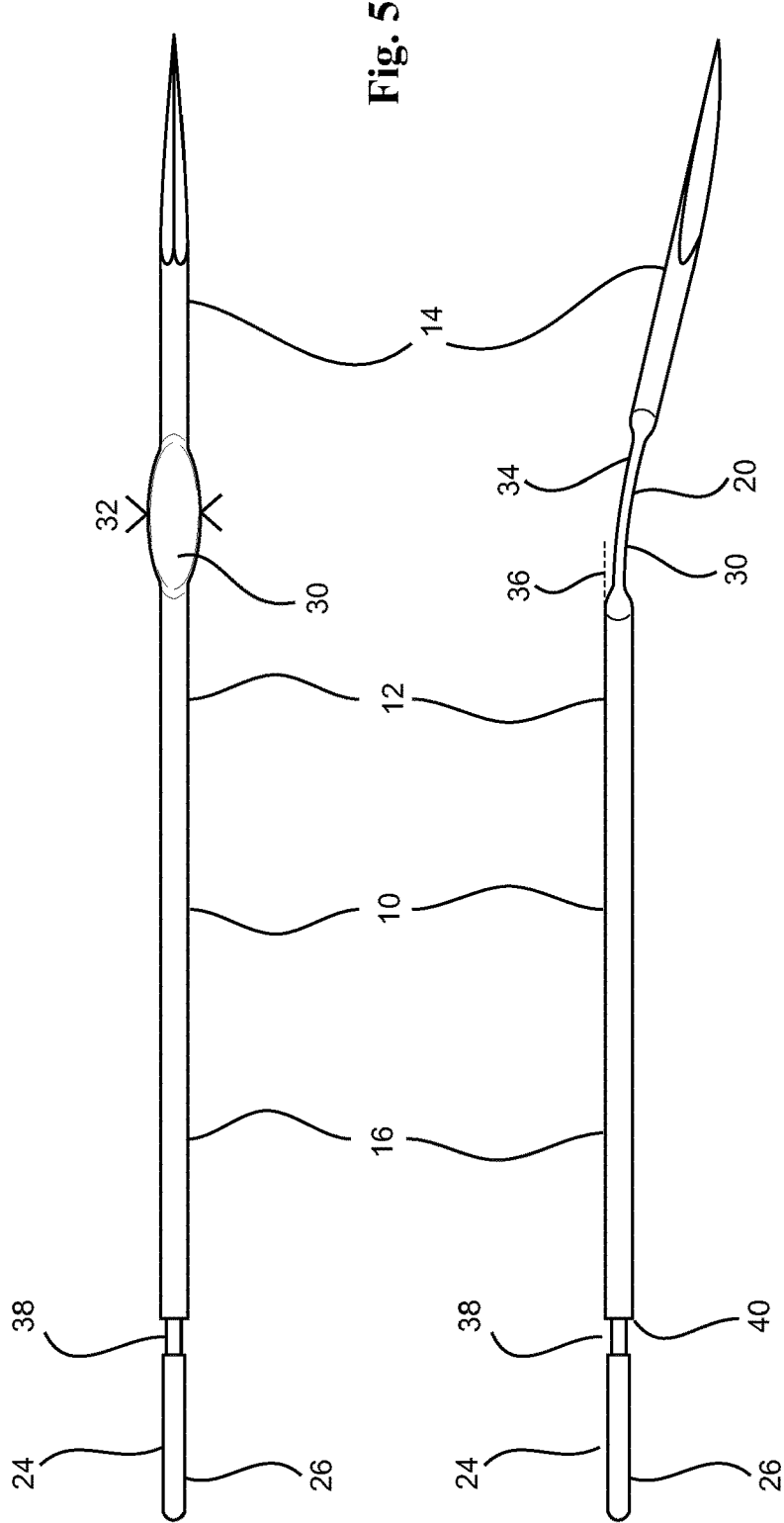

SURGICAL TROCAR

CROSS REFERENCE TO RELATED APPLICATIONS

This application is 371 of PCT Application No. PCT/AU2012/001502, filed Dec. 7, 2012, which is a continuation of Australia 2011905092, filed Dec. 7, 2011. Each of the foregoing applications is hereby incorporated herein by reference in its entirety.

FIELD OF THE INVENTION

The present invention relates to a surgical trocar, such as used introduce a wound drainage tube into a patient to effect closed wound drainage after surgery.

BACKGROUND TO THE INVENTION

Many patients require closed wound drainage after surgery. Closed wound drainage relies on a drainage tube sewn into a wound. The drainage tube extends out of the wound and connects to a source of vacuum, such as a vacuum container with vacuum level control valve. Fluids gathering in the wound after surgery are moved through the drainage tube and collected in the container. A surgical trocar is a stainless steel implement used to introduce the drainage tube into the wound. The surgical trocar typically is a smooth stainless steel shaft with a point at a leading end to pierce skin, and a ridged connector at a trailing end for attachment to the drainage tube. In use, a rear or trailing end of the surgical trocar is attached to a leading end of the drainage tubing. A surgeon then manually uses the surgical trocar to pierce a hole through the skin (and any fat and muscle) of the patient from the internal surface to the outer (epidermal) skin surface. The surgical trocar is then removed from the drainage tubing, often by cutting through the drainage tubing adjacent the surgical trocar.

Because of the natural presence of blood and during surgery, particularly on the gloved hands of the surgeon, the smooth stainless steel shaft of the surgical trocar often becomes slippery and difficult to grip. The slippery surgical trocar rotates in or slips through the surgeon's grip when trying to pierce through the patient's skin and when trying to pull the trocar through from the external side of the skin after initial piercing. This slippage risks injury to the surgeon and delay to the surgical procedure and possible damage to the patient. Attempts have been made to resolve this slippage problem.

Published U.S. Pat. No. 4,490,136 proposes a flattened oblong section straight or angled shaft surgical trocar, the flattened oblong shape aims to reduce the risk of slipping in the surgeon's hands, and the oblong hole produced by the angled sharpened leading end aims to produce a fissure shaped incision. The drainage tube is connected to a barbed spigot at the rear end of the trocar protected by an enlargement that narrows at its leading end and flares out to an enlarged end where the drainage tube connects to the trocar. However, the shaft of this trocar is smooth and does not provide any grip feature on its surface to reduce the likelihood of slipping. Also, the barbed spigot causes the leading end of the drainage tube to flare out to get over the widest part of the barb. Hence, U.S. Pat. No. 4,490,136 proposes the enlarged, portion to compensate for this forced widening and attempts to smoothly and progressively increase the effective width of the trocar, thereby attempting to avoid a step in width, by providing the gradually widening enlargement portion.

Another attempt to reduce the slippage problem has been to provide a series of shallow grip notches across a portion of the width of the straight shaft of the trocar. However, such notches only have limited grip benefit to prevent the trocar from rotating in the surgeon's hand when piercing the skin, and limited grip benefit when trying to push the trocar through the skin.

One known attempt to improve grip on a trocar to introduce a catheter or other tube into a subcutaneous tunnel is disclosed in GB 2103936A. That document discloses a rod or tube having a hand grip at a proximal end and, at a distal end, a detachable tip for passing smoothly through subcutaneous tissue to introduce the catheter or other tube through the tissue wall. Thus, effectively this document discloses a trocar with detachable handle at the end opposite to the detachable working tip or point of the tool. The hand grip is relatively bulky and does not allow for pre-connection of the catheter prior to making an incision into a patient with the tool. This therefore complicates the catheter introduction procedure and requires a separate step of removing the hand grip and attaching the catheter to the proximal end of the rod or tube.

An alternative attempt of providing improved user grip on a trocar is disclosed in U.S. Pat. No. 4,883,474A. That document provides a tube having a stiffened and sharpened end. The stiffened end is a rigid rod extending inside the tube and the rod is shapeable into a grippable shape to assist the user in maneuvering the rod and tube into and through the desired path in the surgical site. Thus, U.S. Pat. No. 4,883,474 teaches the shaping of a rigid rod within tubing to assist in providing grip.

With the above problems in mind, it has been found desirable to provide an improved surgical trocar that improves grip when pushing the trocar through the skin and reduces the likelihood of the trocar rotating in the surgeon's hand at that time.

Reference to any prior art in this specification is not, and should not be taken as, an acknowledgement of any form of admission that the prior art forms part of the common general knowledge in Australia.

SUMMARY OF THE INVENTION

With the aforementioned in view, an aspect of the present invention provides a surgical trocar including an elongate shaft having a first and second shaft portions, the second shaft portion including a leading point or edge for piercing flesh, the shaft further including a curved portion intermediate the first and second shaft portions, the curved portion having an inner and an outer radius, the shaft further including a grip region.

The grip region may include at least one flat zone, preferably integral with the shaft. The integral grip may be provided by at least one flat recess in the shaft.

The grip region may include a machined, stamped or pressed region in the material of the shaft.

At least a portion of the grip region may be located at the inner radius of the curved portion.

The grip region may be or include a thumb grip for a user when pushing the surgical trocar through the skin.

Preferably the shaft has a width and the grip region includes at least one zone that is wider than the width of the shaft. This feature is particularly useful where the shaft is narrow in width, such as under 4.5 mm wide. The grip region can broaden out the width of the shaft, such as an elliptical or oval shaped flared region. Alternatively the grip region is preferably no greater in width than the width of the shaft.

The first shaft portion between the connector and the curved portion may preferably be longer than the second shaft portion between the curved portion and the leading point or edge.

Preferably the second shaft portion is between 30 mm and 80 mm long from the curved portion to a tip of the leading point or edge.

An alternative form of the present invention provides a surgical trocar including an elongate shaft having a first and second shaft portions, the second shaft portion including a leading point or edge for piercing flesh, the first and second shaft portions connected by a curved portion, the curved portion having an inner and an outer radius, the first shaft portion including a connector for receiving a portion of tubing to be introduced into a patient by the trocar, the connector having a continuous surface for contacting a lumen of the tubing.

The connector may be joined to the rest of the first shaft portion by a neck portion with a width less than that of the connector and rest of the first shaft portion. Preferably the connector may have a regular cylindrical outer surface to contact the lumen of the tubing.

BRIEF DESCRIPTION OF THE DRAWINGS

FIGS. 1 and 2 show respective plan and side views of a trocar according to an embodiment of the present invention.

FIGS. 3 and 4 show respective plan and side views of a trocar according to an alternative embodiment of the present invention.

FIGS. 5 and 6 show plan and side views of an alternative embodiment of the present invention.

Figure 7:
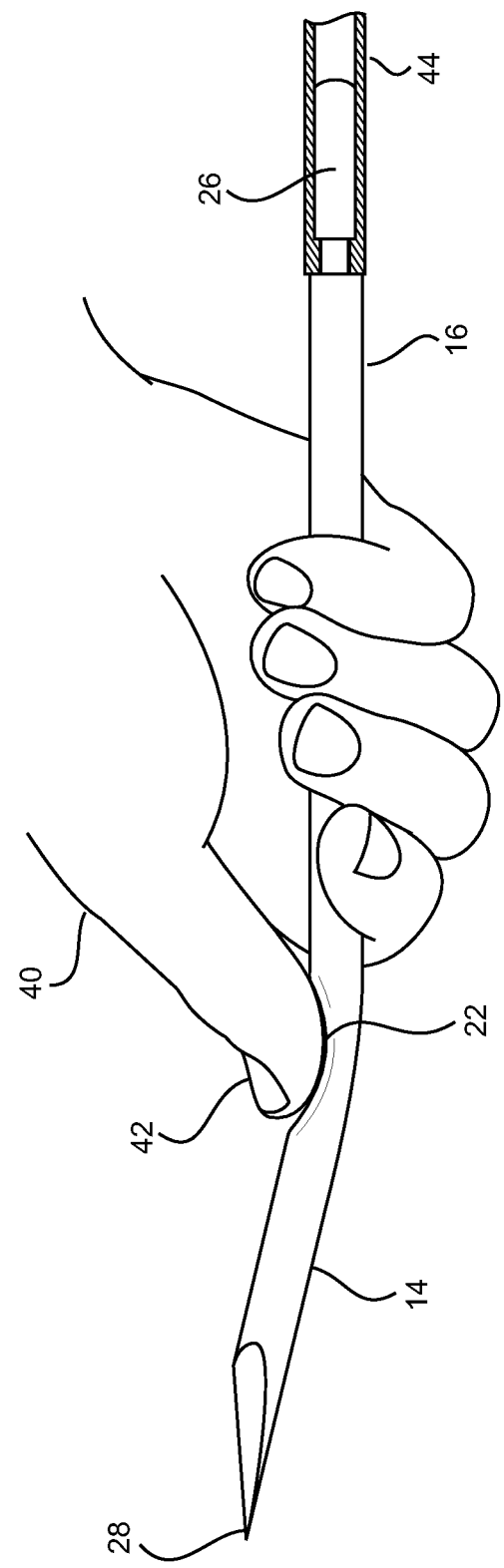
FIGS. 7 and 8 show the trocar of FIGS. 2 and 6 respectively held in a hand of a user with the user's thumb in a grip region.

The invention will now be described with reference to the accompanying figures.

The surgical trocar 10 according to an embodiment of the present invention shown in FIGS. 1 and 2 is of a type to be used for introducing a drainage tube into a wound for closed wound drainage. Once introduced into the wound channel by pushing the trocar through the tissue wall (skin and subcutaneous fat), the proximal end of the tubing is detached from the trocar, often by simply cutting through the tubing, and is sewn into the wound. The distal end of the tubing terminates at a container holding a partial vacuum controlled by a valve. Fluids are drained from the closed wound through the tubing and into the container under the influence of vacuum.

The surgical trocar has a shaft 12 with a first shaft portion 14 and a second shaft portion 16 joined at a curved portion 18. It will be appreciated that the first or second portion of the shaft, or both, may themselves be straight or curved. Preferably, and as shown in FIGS. 1 and 2, the first and second shaft portions are straight, and are connected by a curved intermediate portion. The inner radius 20 of the curved portion includes a flat zone 22 providing a thumb grip region. In use, a user would grip with one hand the first portion of the shaft between the curved portion and the connector 26 at the rear end 24 of the surgical trocar. The user's thumb can then rest on the flat zone 22 in use. When in use, pushing the point 28 through a patient's skin from the body's internal skin surface to the external skin surface, the point usually causes the skin to 'tent' up before piercing through. Substantial effort is required by the user to drive the trocar through the layers of skin (and any fat or other tissues) in order to introduce an attached drainage tube into a wound and allow the drainage tube to exit through the aperture in the skin created by the trocar. If, as is often the case, the user's hands or gloves are wet with blood or other fluids, the trocar can rotate in the user's grip or the user's hand can slide along the shaft of the trocar because sufficient grip friction is not available. The flat area at the inner radius of the curved portion not only gives a larger surface to apply pressure to compared with the curvature of the shaft, but also, because the flat surface is in the inner radius, allows the user to apply forward force and gain additional grip by thumb contact with the leading end of the flat area within the inner radius. Thus, the user not only gains better purchase on the shaft but is also able to apply greater forward force to pierce the skin and have enhanced anti-rotation grip on the trocar.

An alternative embodiment of the present invention is shown in FIGS. 3 and 4. This embodiment has the same features as those of FIGS. 1 and 2; however, the trocar is a different gauge, 19 French, than that of the 16 French gauge of the trocar in FIGS. 1 and 2. Essentially, the shaft 12 is thicker overall.

An alternative embodiment of the surgical trocar of the present invention includes a grip region 30 wider than the width of the shaft 12 of the trocar. As shown in FIGS. 5 and 6, the shaft is narrower than that of the trocar of FIGS. 1 to 4. The grip region is flared out >32<, for example in the form of a 'cobra head', being wider in a middle section of the flat region than the ends thereof which merge into the shaft. This allows a narrow shaft trocar, such as a 10 French gauge trocar, to include features of the present invention without overly thinning the shaft and otherwise making the shaft too weak or bendy. The grip region 30 is formed at the inner radius 20 as provided on the trocars shown in FIGS. 1 to 4. The outer radius 34 may retain the original boundary of the first and second shaft portions, or may be inset or recessed 36, as shown in FIGS. 5 and 6.

Any of the embodiments of the present invention may include a textured surface on the grip region 22,30 for enhanced friction. This may be formed by texturing the metal surface of the trocar or applying a grip material, such as a silicon rubber coating.

As shown in FIGS. 1 to 6, the connector 24 preferably includes a relatively smooth, flat surfaced cylindrical shape to increase contact area with the lumen of the drainage tubing (not shown). The smooth surface increases contact area with the lumen compared to a barbed connector. This improves grip with the tubing, especially with silicon polymer type tubing, and advantageously prevents the tubing from bulging out when fitted over the barb(s) of a connector. Preferably the first shaft portion and the connector have common thinned annular region, such as a groove 38, and the connector is narrower than the width of the first shaft portion, which allows the leading end of the drainage tubing to butt up against a rear end face 40 of the first shaft portion and thereby prevents a bulge. This beneficially reduces the rear end width of the trocar when being pushed/pulled through the piercing in the patient.

In a 19 French gauge trocar embodying the present invention, the connector may be 4.85 mm diameter, the annular recess 3.60 mm diameter and the main shaft 6.35 mm diameter. A 16 gauge trocar embodying the present invention may have a 4.20 mm diameter connector, a 2.75 mm diameter annular recess and a 5.40 mm main shaft. Preferably the first portion of the shaft is within the range 35 mm to 80 mm, though other lengths are considered within the scope of the present invention. The grip region may preferably be at least 15 mm long, preferably between 16 mm and 25 mm.

Advantageously, the grip region givers enhanced anti-rotation control over the trocar, particularly when it is slippery, compared to other round section trocars, and also improves grip when pushing the trocar forward through tissue.

Figure 8:
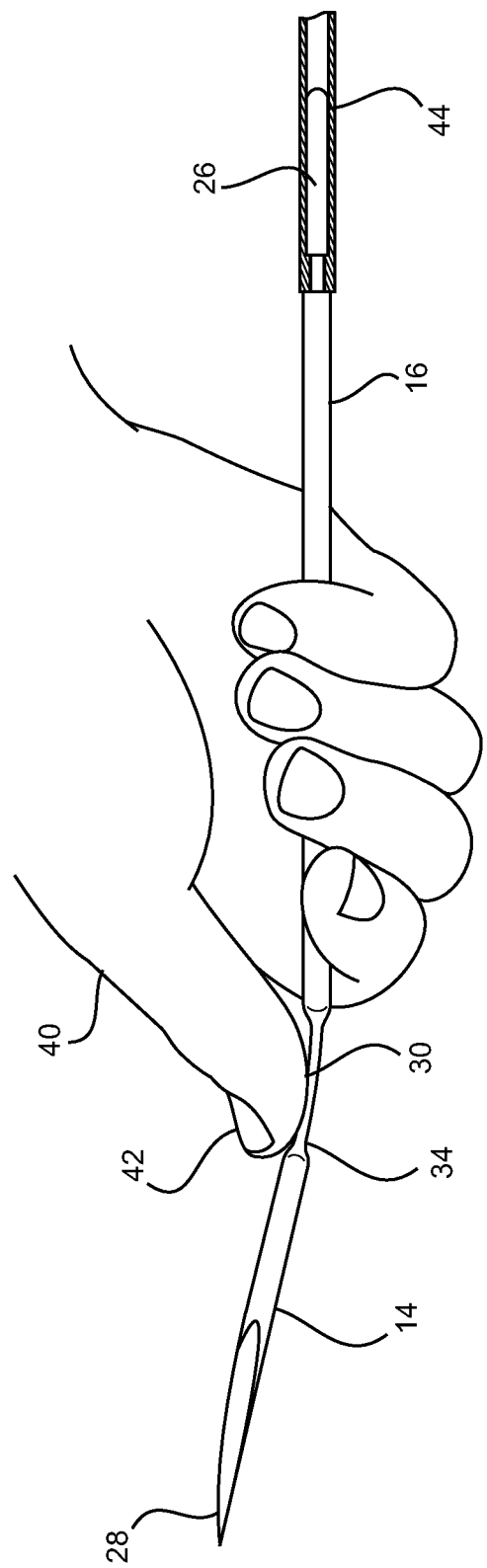

FIGS. 7 and 8 show the trocar of FIGS. 2 and 6 respectively held in a hand 40 of a user with the user's thumb 42 in a grip region 22,30. The user's thumb 42 sits in the recess of the grip region provided at the inner radius of the curve or elbow of the trocar shaft. This thumb grip provides extra control over rotation of the trocar in the user's hand and better grip pushing forward through body tissue. For rotation control, the flatter region in the recess provides increased surface area contact between the user's thumb and the shaft when compared with a standard round section shaft trocar, but maintains the benefit of a circular shaft for finger grip and circular or near circular incision. The drainage tube 44 for the closed wound drain is shown attached to the connector 26. given that the connector is of thinner diameter than the shaft portion 16, the end of the tubing butts against the end of the shaft portion adjacent the annular recess described above.

The invention claimed is:

1. A surgical trocar including an elongate shaft having a first and a second straight shaft portion, the second straight shaft portion including a leading point or edge for piercing flesh, and the shaft further including a curved portion intermediate the first and second straight shaft portions, the curved portion having an inner and an outer radius, the shaft further including an integral thumb grip region, wherein at least a portion of the integral thumb grip region includes a curving recess at the inner radius of the curved portion of the elongate shaft, the first straight shaft portion providing a hand grip for a user and the integral thumb grip region giving a user additional control over rotation and forward force of the leading point of the second straight shaft portion of the trocar by thumb contact with the integral thumb grip region within the inner radius of the curved portion, and the first shaft portion includes a connector for receiving a portion of tubing to be introduced into a patient by the trocar.

2. The surgical trocar as claimed in claim 1, wherein the integral thumb grip region includes at least one flat zone.

3. The surgical trocar as claimed in claim 2, wherein the integral thumb grip region recess includes a machined, stamped or pressed region in the material of the shaft.

4. The surgical trocar as claimed in claim 1, wherein the integral thumb grip region recess includes a machined, stamped or pressed region in the material of the shaft.

5. The surgical trocar as claimed in claim 1, wherein the integral thumb grip region recess is no greater than the width of the elongate shaft.

6. A surgical trocar as claimed in claim 1, wherein the first straight shaft portion is longer than the second straight shaft portion.

7. The surgical trocar as claimed in claim 6, wherein the second straight shaft portion is between 30 mm and 80 mm long from the curved portion to a tip of the point or edge.

8. The surgical trocar as claimed in claim 1, the connector having a continuous surface for contacting a lumen of the tubing.

9. The surgical trocar as claimed in claim 8, wherein the connector is joined to the rest of the first straight shaft portion by a neck portion with a width less than that of the connector and rest of the first straight shaft portion.

10. The surgical trocar as claimed in claim 8, wherein the connector has a regular cylindrical outer surface portion to contact the lumen of the tubing.

11. The surgical trocar as claimed in claim 1, wherein the integral thumb grip region including a flat surface at the inner radius of the curved portion allowing a user to apply force and gain additional grip by thumb contact with a leading end of a flat area within the inner radius.

12. The surgical trocar as claimed in claim 11, wherein the outer radius of the curved portion includes a recess.

13. The surgical trocar as claimed in claim 1, wherein the outer radius of the curved portion includes a recess.

14. The surgical trocar as claimed in claim 1, wherein the integral thumb grip region is recessed as a curving surface that extends into the first straight shaft portion and the second straight shaft portion.

15. The surgical trocar as claimed in claim 1, wherein the curving recess of the integral thumb grip region includes a curved surface.

16. The surgical trocar as claimed in claim 1, wherein the curving recess of the integral thumb grip region is concave.

17. The surgical trocar as claimed in claim 1, including a textured surface on the integral thumb grip region.

18. The surgical trocar as claimed in claim 17, the textured surface provided by texturing a surface of the trocar or by applying a grip material.

19. The surgical trocar as claimed in claim 18, wherein the grip material comprises a silicon rubber coating.

20. The surgical trocar as claimed in claim 1, wherein the connector includes a smooth surfaced cylindrical shape providing contact area with a lumen of the tubing.

21. The surgical trocar as claimed in claim 20, further including a thinned annular region between the first shaft portion and the connector.

22. The surgical trocar as claimed in claim 1, wherein the connector is joined to the first shaft portion by a neck portion with a width less than that of the connector and the first shaft portion.

23. The surgical trocar as claimed in claim 1, wherein the connector is of thinner diameter than the first shaft portion and an end of the tubing butts against an end of the first shaft portion adjacent an annular recess between the connector and the first shaft portion.

* * * * *